United States Patent
Ono et al.

(10) Patent No.: US 6,890,909 B1
(45) Date of Patent: May 10, 2005

(54) BRAIN-PROTECTIVE AGENT

(75) Inventors: Shigeki Ono, Okayama (JP); Isao Date, Okayama (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/446,913

(22) PCT Filed: Jul. 3, 1998

(86) PCT No.: PCT/JP98/03011

§ 371 (c)(1),
(2), (4) Date: Aug. 30, 2000

(87) PCT Pub. No.: WO99/01155

PCT Pub. Date: Jan. 14, 1999

(30) Foreign Application Priority Data

Jul. 4, 1997 (JP) ............................................. 9/180050

(51) Int. Cl.$^7$ ......................... A01N 43/04; A61K 31/70; C12N 15/00; C12N 15/74; C07H 21/04
(52) U.S. Cl. ..................... 514/44; 424/450; 435/320.1; 536/24.1
(58) Field of Search ....................... 514/44, 2; 424/450; 435/320.1; 536/24.1

(56) References Cited

U.S. PATENT DOCUMENTS 6,410,516 B1    6/2002   Baltimore et al. ............. 514/44

FOREIGN PATENT DOCUMENTS

EP   0 824 918 A    2/1998
WO   WO 96/35430   11/1996

OTHER PUBLICATIONS

Crystal Transfer of genes to humans: early lessons and obstacles to success pp. 404–410 vol. 270 1995.*
Miller et al. Progress in transcriptionally targeted and regulatable vectors for genetic therapy pp. 803–815 1997.*
Deonararain ligand–targeted receptor–mediated vectors for gene delivery pp. 53–69 1998.*
Orkin et al. Report and recommendations of the panel to assess the NIH investment in research on gene therapy Dec. 7, 1995.*
Friedmann Overcoming the obstacles pp. 96–101 Jun. 1997.*
Verma et al. Gene therapy promises, problems and prospects pp. 239–242.*

* cited by examiner

Primary Examiner—Anne-Marie Falk
(74) Attorney, Agent, or Firm—Oblon, Spivak, McClelland, Maier & Neustadt, P.C.

(57) ABSTRACT

A brain-protective agent containing an NF-κB decoy. In brain diseases, the brain can be particularly effectively protected against brain disorders (for example, cerebral vasospasm following a subrachnoidal hemorrhage and apoptosis of the nerve cells following a cerebrovasucular accident or serious head injury) caused by the undesired activation of cytokines or cell adhesion factors which are regulated by NF-κB by administering the brain-protective agent containing an NF-κB decoy, i.e., acompound antadonistic specifically to a nucleic acid to which NF-κB binds.

16 Claims, No Drawings

BRAIN-PROTECTIVE AGENT

TECHNICAL FIELD

This invention relates to a brain-protective agent comprising an NF-κB decoy, particularly a brain-protective agent for the brain disorder associated with encephalopathy. More particularly, the invention relates to a brain-protective agent comprising an NF-κB decoy for brain disorders arising from encephalopathy and to a method of protecting the brain which comprises using a brain-protective agent comprising said decoy.

BACKGROUND ART

The transcription factor NF-κB is considered to be related to various diseases such as ischemic, inflammatory and autoimmune diseases, and it is expected that administration of its decoy will be effective in the therapy and prophylaxis of such diseases (WO 96/35430). The transcription factor NF-κB is a heterodimeric complex of p65 and p50 proteins. This factor usually exists in the form of a complex with the inhibitor protein IκB in the cytoplasm and, as such, is prevented from migrating to the nucleus. However, when exposed to a stimulus such as cytokines, ischemia or reperfusion for whatever reason, the IκB is phosphorylated and hydrolyzed so that the NF-κB is activated and finds its way into the nucleus. NF-κB binds to the NF-κB binding sites on the chromosomes and promotes transcription of the downstream genes. The genes regulated by NF-κB include but are not limited to those encoding cytokines such as IL-1, IL-6, IL-8 and adhesion factors such as VCAM-1 and ICAM-1.

Meanwhile, with regard to encephalopathy, it is known that brain disorders occur from various causes including neuronal death and, therefore, the need for brain-protection has been felt in recent years.

For example, the success rate in the treatment of subarachnoidal hemorrhage originating from a ruptured cerebral aneurysm has increased dramatically since the advent of the operating microscope made aneurysmal clipping a safe operation. However, as to brain disorders such as the cerebral vasospasm following subarachnoid hemorrhage, the mechanisms of onset remain to be elucidated and no effective therapeutic modalities have been established yet.

DISCLOSURE OF INVENTION

The inventors of this invention predicted that activation of the production of cytokines and cell adhesion factors which are under regulation by NF-κB is one of the causes for triggering brain disorders associated with encephalopathy (for example, the cerebral vasospasm following a subarachnoidal hemorrhage and apoptosis of the nerve cells following a cerebrovascular accident or serious head injury) and did intensive investigations. As a result, they discovered that for protection of the brain against brain disorders associated with encephalopathy, it is especially effective to administer an NF-κB decoy, that is to say a compound specifically competing with the nucleic acids to which NF-κB binds, and ultimately developed this instant invention.

This invention, therefore, provides a brain-protective agent containing an NF-κB decoy and more particularly to a brain-protective agent for brain disorders associated with encephalopathy which comprises an NF-κB decoy and a method for brain-protection.

The disease or disorder in which the brain-protective agent of this invention can be indicated is not particularly restricted but, in view of the fact that it is particularly effective in brain tissues against disorders caused by unwanted activation of the genes which are under regulation by the transcription factor NF-κB, it can be used in the cerebral vasospasm following subarachnoid hemorrhage, cerebral infarcts in cerebral thrombosis and cerebral embolism, sequelae of intracranial hemorrhage, cerebrovascular dementia, hydrocephalus, cerebral arterial anomaly-angioma, various brain tumors, Parkinson's syndrome, cerebral arteriosclerosis, meningitis (e.g. bacterial, aseptic and postoperative), encephalitis, AIDS, various types of encephalopathy (Behçet's disease disease, multiple sclerosis) and brain disorders arising from neuronal death caused by serious head trauma. The brain-protective agent comprising an NF-κB decoy which is provided by this invention is particularly suitable for the therapy and prophylaxis of cerebral vasospasm which appears in association with subarachnoid hemorrhage.

The NF-κB decoy for use in this invention need only be a substance which inhibits the activation of genes by NF-κB, more particularly a compound which specifically antagonizes the NF-κB binding sites of nucleic acid on the chromosomes, thus including a nucleic acid and an analog thereof, among others (WO 96/35430, JP 07-291860A). The preferred example of said NF-κB decoy is an oligonucleotide containing a consensus sequence of the NF-κB binding site, a mutant thereof or a compound containing either of them within its molecule. The oligonucleotide mentioned above may be a DNA or an RNA, or may contain a modified nucleotide or/and a pseudonucleotide. Furthermore, said oligonucleotide, said mutant or said compound containing either of them within the molecule may be single-stranded or double-stranded, and linear or cyclic. The mutant means a nucleic acid representing a partial mutation, substitution, insertion or deletion of the sequence, which specifically antagonizes the binding sites of nucleic acid to which NF-κB binds. The if still more preferred NF-κB decoy is a double-stranded oligonucleotide containing one or several units of said nucleotide sequence or a mutant thereof. The oligonucleotide for use in this invention includes such as an oligonucleotide (S-oligo) containing thiophosphodiester bonds available upon substitution of a sulfur atom for the oxygen atom of the phosphodiester linkage or a modified oligonucleotide in which a methyl phosphate group carrying no electric charge has been substituted for the phosphodiester bond, as modified to make an oligonucleotide hardly susceptible to decomposition in vivo.

The technology which can be used for the production of the NF-κB decoy for use in this invention includes general methods for chemical synthesis or biochemical synthesis. For example, when a nucleic acid is used as the NF-κB decoy, the nucleic acid synthesizing techniques which are generally used in genetic engineering can be used. For example, the objective decoy nucleotide can be directly synthesized by using a DNA synthesizer or such a nucleic acid, a nucleic acid containing said nucleic acid or a fragment thereof may be synthesized and, then, amplified by PCR or using a cloning vector, for instance. Furthermore, the nucleic acid thus obtained may be digested with restriction enzymes and a ligation reaction may be carried out with a DNA ligase or the like to provide the objective nucleic acid. In addition, for securing the decoy nucleotide which is more stable in the cell, the base, pentose or phosphoric acid moiety of the nucleic acid may be chemically modified, for example by way of alkylation or acylation.

The pharmaceutical composition comprising the NF-κB decoy as an active ingredient in accordance with this invention is not particularly restricted only if the active ingredient may be taken up in the lesioned cell or in the target tissue cells. Thus, the NF-κB decoy can be administered, either as it is or as mixed with a routine carrier, orally, parenterally, topically or in an external application form. The pharmaceutical composition may take a liquid dosage form such as a solution, a suspension, a syrup, a liposomal preparation, an emulsion or a syrup or a solid dosage form such as tablets, granules, powders and capsules. Where necessary, those preparations may be supplemented with various carriers, auxiliary agents, stabilizers, lubricants and other routine additives, for example lactose, citric acid, tartaric acid, stearic acid, magnesium stearate, terra alba, sucrose, corn starch, talc, gelatin, agar, pectin, peanut oil, olive oil, cacao butter and ethylene glycol.

The particularly preferred and advantageous preparations in the case of using a nucleic acid or a modification product thereof as the NF-κB decoy are the forms which are in common use in the gene transfer technology, for example liposomes such as a membrane-fusion liposome preparation using Sendai virus and the liposomes utilizing endocytosis, preparations containing a cationic lipid such as lipofectoamine (Life Tech Oriental), Tfx50 or the like and viral preparations using a retrovirus vector, an adenovirus vector or the like.

The liposome structure of such liposomal preparations may be any of the large unilamellar vesicle (LUV) structure, multilamellar vesicle (MLV) structure, and small unilamellar vesicle (SUV) structure. While the vesicle size may be 200~10000 nm for LUV, 400~3500 nm for MLV, and about 20~50 nm for SUV, it is preferable, in the case of a membrane-fusion liposomal preparation using Sendai virus, to employ an MLV system of 200~1000 nm.

The technology for producing liposomes is not particularly restricted only provided that the decoy can be entrapped and held therein. Thus, the objective liposomes can be produced by the conventional methods, for example the reverse phase evaporation method (Szoka, F., et al: Biochim. Biophys. Acta, Vol. 601 559 (1980)), ether injection method (Deamer, D. W.: Ann. N. Y. Acad. Sci., Vol. 308 250 (1978)), and surfactant method (Brunner, J., et al: Biochim. Biophys. Acta, Vol. 455 322 (1976)).

The lipid generally used for the formation of a liposomal structure includes phospholipids, cholesterols and nitrogen-containing lipids but phospholipids are preferred. Thus, native phospholipids such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, lysolecithin, etc., hydrogenation products thereof, which can be obtained by the conventional method, and synthetic phospholipids such as dicetylphosphate, distearoyl phosphatidylcholine, dipalmitoyl phosphatidylcholine, dipalmitoyl phosphatidyl ethanolamine, dipalmitoyl phosphatidylserine, eleostearoylphosphatidylcholine, eleostearoyl phosphatidylethanolamine, eleostearoyl phosphatidylserine, etc. can be employed.

The lipids inclusive of those phospholipids can be used each independently but may be used in a combination of two or more species. In this connection, by using a lipid having a positively charged group-containing moiety within the molecule, such as ethanolamine or choline, the binding rate of a decoy nucleotide which is negatively charged can be increased. In addition to the major component phospholipid, various additives such as cholesterol compounds, stearylamine and/or α-tocopherol, all of which are known as liposome additives, can be used in the formation of said liposomes.

To the liposomes thus obtained, there can be added a membrane fusion promoter, for example Sendai virus, inactivated Sendai virus, a membrane fusion promoting protein purified from Sendai virus, or polyethylene glycol, can be added for promoting the intracellular uptake by the lesioned cells or target tissue cells.

A typical procedure for the production of liposomes is now described specifically. A typical procedure comprises dissolving the above-described liposome component material and said cholesterol and/or the like in an organic solvent such as tetrahydrofuran, chloroform, ethanol or the like, placing the solution in a suitable vessel and removing the solvent by distillation under reduced pressure to form a membrane of the liposome component material. To this is added a buffer containing the NF-κB decoy, followed by stirring. To the liposomes thus obtained is added said membrane fusion promoter, which is optional, and the liposomes are isolated. The NF-κB decoy-containing liposomes thus obtained are suspended in a suitable buffer or first lyophilized and then redispersed in a suitable solvent for use in the therapy. The membrane fusion promoting substance may be added during the interim period between isolation of liposomes and use.

The decoy content of the resulting preparation containing the NF-κB decoy as a main component can be judiciously selected according to the disease to be treated, target site, dosage form and method of administration.

The NF-κB decoy-containing brain-protective agent can be administered by a variety of alternative methods according to the type of disease and the kind of decoy used. For example, it can be injected into the cistern (subarachnoid administration).

The dosage of the NF-κB decoy should be judiciously selected according to the patient's age and other factors, the type of disease and the kind of decoy used, among other factors, but for intracisternal administration, for instance, 10~10,000 nmoles per dose can be administered at a judicious timing.

The following example is intended to illustrate this invention in further detail.

EXAMPLES

Construction of the Animal Model

As experimental animals, male New Zealand White rabbits weighing 2~2.5 kg were used. Each experimental animal was anesthetized with pentobarbital, 20 mg/kg i.v. The auricular artery was cannulated and the arterial blood was harvested. The head was then immobilized in a stereotaxic frame and the atlanto-occipital membrane was exposed by inducing contraction of the nuchal muscle After 1 ml of cerebrospinal fluid was aspirated off, 1 mg/kg of autologous blood was carefully injected into the cistern (subarachnoid space) over not less than 3 minutes using a 27 G needle. Then, the animal's head was tilted down and kept in that position for 30 minutes so as to flood the basilar artery with the animal's autologous blood for the construction of a subarachnoid hemorrhage model. Administration of the decoy A rabbit NF-kB binding recognition sequence (20 mer; TGGAGGGGCTTTCCCCATAG) (SEQ ID NO: 1) (NF-kB decoy group) and a scrambled NF-kB binding recognition sequence (20 mer) (scramble decoy group) were synthesized (Ray, A., Gao, X. & Ray, B. J. Biol. Chem. 270, 29201–29208 (1995)) and, using a cationic liposomal delivery system (Tfx50, Promega, Wis. U.S.A.), those oligonucleotides were respectively administered into the cistern two days before the construction of subarachnoid hemorrhage.

For evaluation, angiography was performed 3 days before and 4 days after the construction of subarachnoid hemorrhage and the percent change in diameter of the basilar artery was determined. In addition, a histological investigation using hematoxylin-eosin staining was carried out. NF-κB activity was evaluated by gel shift assay.

Results

Cerebral angiography revealed constrictions down to 69% in the control group and scrambled decoy group but a marked inhibition of vascular narrowing to about 90% in the NF-κB group. Histologically, too, whereas marked decreases in the vascular diameter were found in the control group and scrambled decoy group, the histological picture in the NF-κB group was almost similar to that of the normal vessel. In gel shift assay, a definite inhibition of activity was noted in the NF-κB decoy group compared with the control group.

What is claimed is:

1. A method for diminishing a cerebral vasospasm associated with a subarachnoid hemorrhage comprising administering to a subject in need thereof an effective amount of a composition comprising:

an oligonucleotide or modified oligonucleotide comprising the base sequence of SEQ ID NO: 1 and
   a liposomal delivery system, wherein said oligonucleotide or modified oligonucleotide is double-stranded.

2. The method of claim 1, wherein said composition is administered intracisternally.

3. The method of claim 1, wherein said liposomal delivery system is a cationic liposomal delivery system.

4. The method of claim 1, wherein said liposome delivery system comprises a membrane fusion promoter.

5. The method of claim 1, wherein said oligonucleotide or modified oligonucleotide comprising the base sequence of SEQ ID NO: 1 is a cyclic oligonucleotide or modified oligonucleotide.

6. The method of claim 1, wherein said composition comprises an oligonucleotide comprising the base sequence of SEQ ID NO: 1 which is DNA.

7. The method of claim 1, wherein said composition comprises a modified oligonucleotide comprising the base sequence of SEQ ID NO: 1.

8. The method of claim 1, wherein said composition comprises an S-oligonucleotide, an oligonucleotide in which one or more methyl phosphate group(s) carrying no charge has (have) been substituted for the phosphodiester bond, an acylated oligonucleotide, or an alkylated oligonucleotide, comprising the base sequence of SEQ ID NO: 1.

9. The method of claim 1, wherein said oligonucleotide or modified oligonucleotide comprises more than one units of the base sequence of SEQ ID NO: 1.

10. The method of claim 1, wherein said oligonucleotide or modified oligonucleotide comprises an individual unit of the base sequence of SEQ ID NO: 1.

11. A liposome comprising oligonucleotide or modified oligonucleotide comprising the base sequence of SEQ ID NO: 1, wherein said oligonucleotide or modified oligonucleotide is double-stranded.

12. The liposome of claim 11 that comprises a cationic lipid.

13. The liposome of claim 11 that comprises a membrane-fusion promoter.

---

SEQUENCE LISTING

<160> NUMBER OF SEQ ID NOS: 1

<210> SEQ ID NO 1
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
tggaggggct ttccccatag                    20

14. The liposome of claim 11 that comprises a large unilamellar vesicle (LUV) structure.

15. The liposome of claim 11 that comprises a multilamellar vesicle (MLV) structure.

16. The liposome of claim 11 that comprises a small unilamellar vesicle (SUV) structure.

* * * * *